US012527936B2

(12) United States Patent
Schabert et al.

(10) Patent No.: US 12,527,936 B2
(45) **Date of Patent: *Jan. 20, 2026**

(54) GUIDEWIRE AND MEDICAL DEVICE INCLUDING LASER CUT TUBE

(71) Applicant: Deepin Technologies, LLC, San Jose, CA (US)

(72) Inventors: Jon Schabert, San Jose, CA (US); Jiaxu Wang, San Jose, CA (US); Alex Kubacki, San Jose, CA (US)

(73) Assignee: Deepin Technologies, LLC, San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/315,517

(22) Filed: Aug. 30, 2025

(65) Prior Publication Data

US 2025/0387591 A1 Dec. 25, 2025

Related U.S. Application Data

(63) Continuation of application No. 18/963,683, filed on Nov. 28, 2024.

(60) Provisional application No. 63/610,697, filed on Dec. 15, 2023.

(51) Int. Cl.

| | |
|---|---|
| ***A61B 5/00*** | (2006.01) |
| ***A61M 25/00*** | (2006.01) |
| ***A61M 25/01*** | (2006.01) |
| *A61M 25/09* | (2006.01) |

(52) U.S. Cl.

CPC .... *A61M 25/0013* (2013.01); *A61M 25/0074* (2013.01); *A61M 25/0138* (2013.01); *A61M 2025/09108* (2013.01); *A61M 2025/09175* (2013.01); *A61M 2207/10* (2013.01)

(58) Field of Classification Search

CPC .......... A61M 25/0013; A61M 25/0074; A61M 25/0138; A61M 2025/09108; A61M 2025/09175; A61M 2207/10

See application file for complete search history.

(56) References Cited

U.S. PATENT DOCUMENTS

| | | | |
|---|---|---|---|
| 1,065,018 | A | 6/1913 | Barber |
| 5,911,717 | A | 6/1999 | Jacobsen |
| 6,014,919 | A | 1/2000 | Jacobsen |
| 6,017,319 | A | 1/2000 | Jacobsen |
| 6,022,369 | A | 2/2000 | Jacobsen |
| 6,063,101 | A | 5/2000 | Jacobsen |
| 6,183,410 | B1 | 2/2001 | Jacobsen |
| 6,214,042 | B1 | 4/2001 | Jacobsen |
| 6,302,870 | B1 | 10/2001 | Jacobsen |
| 6,428,489 | B1 | 8/2002 | Jacobsen |
| 6,440,088 | B1 | 8/2002 | Jacobsen |
| 6,478,778 | B1 | 11/2002 | Jacobsen |

(Continued)

*Primary Examiner* — May A Abouelela
(74) *Attorney, Agent, or Firm* — Deepin IP

(57) ABSTRACT

A guidewire device includes an elongate core wire and a tube member over the distal section of the elongate core wire. The tube member comprises a plurality of transverse cuts at a plurality of axial locations of the tube member, forming a plurality of circumferentially extending rings joined by a plurality of beams. The plurality of transverse cuts comprises a tapered geometry with a cut width at the outer surface of the tube member being greater than a cut width at the inner surface of the tube member.

12 Claims, 9 Drawing Sheets

(56) References Cited

U.S. PATENT DOCUMENTS 7,833,175 B2* 11/2010 Parins .................. A61M 25/09 604/524
7,833,564 B2 11/2010 Chen
7,878,984 B2 2/2011 Jacobsen
7,914,466 B2 3/2011 Davis
7,914,467 B2 3/2011 Layman
8,048,004 B2 11/2011 Davis
8,257,279 B2 9/2012 Davis
8,376,961 B2 2/2013 Layman
8,419,658 B2 4/2013 Eskuri
8,460,213 B2 6/2013 Northrop
8,551,021 B2 10/2013 Voeller
8,556,914 B2 10/2013 Vrba
8,784,337 B2 7/2014 Voeller
8,795,202 B2 8/2014 Northrop
8,870,790 B2 10/2014 Davis
8,900,163 B2 12/2014 Jacobsen
8,915,865 B2 12/2014 Jacobsen
8,932,235 B2 1/2015 Jacobsen
8,936,558 B2 1/2015 Jacobsen
8,939,916 B2 1/2015 Jacobsen
9,067,332 B2 6/2015 Lippert
9,067,333 B2 6/2015 Lippert
9,072,873 B2 7/2015 Lippert
9,072,874 B2 7/2015 Northrop
9,227,037 B2 1/2016 Northrop
9,375,234 B2 6/2016 Vrba
9,616,195 B2 4/2017 Lippert
9,636,115 B2 5/2017 Henry
9,662,798 B2 5/2017 Christian
9,950,137 B2 4/2018 Lippert
10,232,141 B2 3/2019 Christian
10,315,007 B2 6/2019 Chan
10,363,389 B2 7/2019 Lippert
10,722,690 B2 7/2020 McGowan
10,821,268 B2 11/2020 Snyder
10,953,202 B2 3/2021 Lippert
10,953,203 B2 3/2021 Lippert
10,980,968 B2 4/2021 Christian
11,052,228 B2 7/2021 Lippert
11,207,502 B2 12/2021 Lippert
11,253,277 B2 2/2022 Buck
11,259,821 B2 3/2022 Buck
11,369,351 B2 6/2022 Davis
11,406,791 B2 8/2022 Lippert
11,420,022 B2 8/2022 Northrop
11,439,799 B2 9/2022 Buck
11,452,541 B2 9/2022 Lippert
11,457,936 B2 10/2022 Buck
11,819,228 B2 11/2023 Buck
11,890,434 B2 2/2024 Lippert
11,896,781 B2 2/2024 Northrop
11,951,267 B2 4/2024 Lippert
12,011,555 B2 6/2024 Davis
12,115,324 B2 10/2024 Lippert
12,178,975 B2 12/2024 Lippert
12,220,538 B2 2/2025 Lippert
2002/0082499 A1 6/2002 Jacobsen
2003/0009208 A1 1/2003 Snyder
2004/0111044 A1 6/2004 Davis
2004/0181174 A2 9/2004 Davis
2007/0282358 A1* 12/2007 Remiszewski ....... A61B 1/0057 606/159
2007/0287955 A1 12/2007 Layman
2008/0021347 A1 1/2008 Jacobsen
2008/0021348 A1 1/2008 Jacobsen
2008/0021400 A1 1/2008 Jacobsen
2008/0021401 A1 1/2008 Jacobsen
2008/0021402 A1 1/2008 Jacobsen
2008/0021403 A1 1/2008 Jacobsen
2008/0021404 A1 1/2008 Jacobsen
2008/0021405 A1 1/2008 Jacobsen
2008/0021406 A1 1/2008 Jacobsen
2008/0021407 A1 1/2008 Jacobsen
2008/0021408 A1 1/2008 Jacobsen
2008/0077119 A1 3/2008 Snyder
2008/0097247 A1 4/2008 Eskuri
2008/0125753 A1 5/2008 Chen
2008/0147170 A1 6/2008 Vrba
2008/0262474 A1 10/2008 Northrop
2009/0036832 A1 2/2009 Skujins
2009/0177119 A1 7/2009 Heidner
2009/0177185 A1 7/2009 Northrop
2009/0254000 A1 10/2009 Layman
2010/0063479 A1 3/2010 Merdan
2010/0145308 A1 6/2010 Layman
2010/0256527 A1 10/2010 Lippert
2010/0256528 A1* 10/2010 Lippert ................. A61M 25/09 600/585
2010/0256601 A1* 10/2010 Lippert ............. A61M 25/0051 604/523
2010/0256602 A1 10/2010 Lippert
2010/0256603 A1 10/2010 Lippert
2010/0256604 A1 10/2010 Lippert
2010/0256605 A1 10/2010 Lippert
2010/0256606 A1* 10/2010 Lippert ............. A61M 25/0051 604/524
2011/0245808 A1* 10/2011 Voeller .............. A61M 25/0054 604/528
2012/0203207 A1 8/2012 Northrop
2012/0289938 A1 11/2012 Northrop
2013/0267913 A1 10/2013 Northrop
2014/0039532 A1 2/2014 Vrba
2014/0052107 A1 2/2014 Voeller
2014/0336620 A1 11/2014 Layman
2016/0015935 A1 1/2016 Chan
2017/0182295 A1 6/2017 McGowan
2017/0189643 A1 7/2017 Christian
2017/0203076 A1* 7/2017 Groneberg ........ A61M 25/0054
2017/0281909 A1* 10/2017 Northrop .......... A61M 25/0013
2018/0015261 A1 1/2018 Lippert
2018/0015262 A1 1/2018 Lippert
2018/0015263 A1 1/2018 Lippert
2018/0071496 A1 3/2018 Snyder
2018/0177517 A1* 6/2018 Lippert .............. A61B 17/3207
2018/0193607 A1 7/2018 Lippert
2019/0105463 A1 4/2019 Christian
2019/0160259 A1* 5/2019 Cottone ............ A61M 25/0054
2019/0184143 A1* 6/2019 Onushko .......... A61B 17/22031
2019/0255290 A1* 8/2019 Snyder .............. A61M 25/0054
2019/0262598 A1 8/2019 Mock
2019/0290883 A1 9/2019 Lippert
2020/0094027 A1 3/2020 Davis
2020/0121308 A1 4/2020 Davis
2020/0222672 A1 7/2020 Davis
2020/0345975 A1 11/2020 Snyder
2021/0008351 A1 1/2021 Snyder
2021/0128885 A1 5/2021 Lu
2021/0162184 A1 6/2021 Lippert
2021/0178127 A1 6/2021 Gerberding
2021/0178128 A1 6/2021 Lippert
2021/0186536 A1 6/2021 Buck
2021/0186537 A1 6/2021 Buck
2021/0186542 A1 6/2021 Buck
2021/0187244 A1 6/2021 Buck
2021/0213241 A1 7/2021 Christian
2021/0228845 A1* 7/2021 Lippert ........... A61M 25/09041
2021/0275779 A1 9/2021 Northrop
2021/0282759 A1 9/2021 Layman
2021/0283372 A1 9/2021 Murphy
2021/0283380 A1 9/2021 Lippert
2021/0315596 A1 10/2021 Buck
2021/0315597 A1 10/2021 Buck
2021/0315598 A1 10/2021 Buck
2021/0316121 A1 10/2021 Buck
2021/0316127 A1 10/2021 Buck
2021/0346656 A1 11/2021 Lippert
2022/0105312 A1* 4/2022 Davis ................ A61M 25/0053
2022/0105318 A1 4/2022 Davis
2022/0211981 A1* 7/2022 Darbellay ......... A61M 25/0147
2022/0280147 A1 9/2022 Davis
2022/0296850 A1* 9/2022 Lippert ............. A61M 25/0054
2022/0338718 A1* 10/2022 Van Ness ............. A61B 1/0055
2022/0378459 A1 12/2022 Lippert

(56) References Cited

U.S. PATENT DOCUMENTS

| | | | | |
|---|---|---|---|---|
| 2022/0401699 | A1 | 12/2022 | Northrop | |
| 2023/0015259 | A1 | 1/2023 | Buck | |
| 2023/0046468 | A1 | 2/2023 | Lau | |
| 2023/0047098 | A1 | 2/2023 | Lau | |
| 2023/0048055 | A1 | 2/2023 | Lau | |
| 2023/0048388 | A1 | 2/2023 | Lau | |
| 2023/0052862 | A1 | 2/2023 | Lau | |
| 2023/0082226 | A1 * | 3/2023 | Lippert | A61M 25/09<br>604/164.13 |
| 2023/0191014 | A1 * | 6/2023 | Yokoyama | A61M 25/005<br>604/6.16 |
| 2023/0405270 | A1 * | 12/2023 | McGuinn | A61F 2/958 |
| 2024/0032949 | A1 | 2/2024 | Yang | |
| 2024/0033019 | A1 | 2/2024 | Lau | |
| 2024/0033475 | A1 * | 2/2024 | Sirhan | A61B 17/22 |
| 2024/0033486 | A1 | 2/2024 | Lau | |
| 2024/0041491 | A1 * | 2/2024 | Patel | A61B 17/320758 |
| 2024/0108210 | A1 * | 4/2024 | Hamm | A61B 1/00165 |
| 2024/0123196 | A1 | 4/2024 | Lippert | |
| 2024/0181207 | A1 | 6/2024 | Bartholomew | |
| 2024/0181208 | A1 | 6/2024 | Bartholomew | |
| 2024/0181209 | A1 | 6/2024 | Bartholomew | |
| 2024/0181224 | A1 | 6/2024 | Bartholomew | |
| 2024/0183382 | A1 | 6/2024 | Bartholomew | |
| 2024/0198039 | A1 * | 6/2024 | Wainwright | A61M 25/0108 |
| 2024/0198059 | A1 | 6/2024 | Lippert | |
| 2024/0207570 | A1 | 6/2024 | Mar | |
| 2024/0207577 | A1 | 6/2024 | Pope | |
| 2024/0216653 | A1 | 7/2024 | Pope | |
| 2024/0299710 | A1 | 9/2024 | Davis | |
| 2024/0342444 | A1 | 10/2024 | Lippert | |
| 2024/0390639 | A1 | 11/2024 | Lesueur | |
| 2025/0108193 | A1 * | 4/2025 | Khan | A61M 25/09 |

* cited by examiner

GUIDEWIRE AND MEDICAL DEVICE INCLUDING LASER CUT TUBE

CROSS-REFERENCE TO RELATED APPLICATIONS

This application is a continuation of U.S. application Ser. No. 18/963,683 filed Nov. 28, 2024 entitled "Guidewire and Medical Device including Laser Cut Tube," which claims priority to U.S. provisional patent application No. 63/610,697 filed Dec. 15, 2023 entitled "Guidewire and Medical Device including Laser Cut Tube," the disclosure of which is hereby incorporated by reference in its entirety.

TECHNICAL FIELD

This application relates generally to medical devices and methods of making and using medical devices to treat diseases. Particularly, various embodiments of a guidewire device and a method of making the same are described.

BACKGROUND

Guidewires are widely used in the medical field for guiding a device to a particular location in a patient's body to perform delicate procedures e.g., guiding a catheter deep in the vasculature of the body. Guidewires often require a variable stiffness profile, typically with the most flexible section at the distal end while maintaining good torque transmission for trackability and delivery in tortuous anatomy. It is important to ensure that the tip of a guidewire can be bent to a tight radius to impart a curved shape that assists with vessel selection.

A guidewire generally includes a core wire, which may have a tapered distal section reinforced with a structure joined to an atraumatic tip. Traditionally, metal coils are used as guidewire reinforcement. As micro-machining technology has evolved, micro-machined hypotubes also entered the field as device components. However, micro-machining techniques are limiting in processing speed, cutting geometries and lengths that can be imparted on the hypotube due to the size and shape of the cutting element.

Therefore, while advancement has been made in the field of guidewire devices, there is still a general need for improvement to overcome these and other problems experienced by the conventional techniques. It would be desirable to provide a new technique to attain cutting geometries on a guidewire device that can balance the complex requirements of bending flexibility, tensile strength, and torque transmission for various medical applications, and allow the guidewire tip to reach a tight bending radius without kinking.

SUMMARY

In one aspect, embodiments of the disclosure feature a guidewire device. In general, an embodiment of the guidewire device comprises an elongate core wire and a tube member over the distal section of the elongate core wire. The tube member comprises a plurality of transverse cuts at a plurality of axial locations of the tube member, forming a plurality of circumferentially extending rings joined by a plurality of beams. The plurality of transverse cuts comprises a tapered geometry with a cut width at the outer surface of the tube member being greater than a cut width at the inner surface of the tube member.

In various embodiments of the aspect, the tapered geometry of at least one of the plurality of transverse cuts comprises a taper angle (X) that satisfies the following equation:

$$X = 2\ \arcsin[(c/2)/(r - b/2)]$$

wherein c represents the cut width of the at least one of the plurality of the transverse cuts at the inner surface, r represents an inner radius of the tube member, and b represents a beam height of the beam adjacent to the at least one of the plurality of the transverse cuts.

In various embodiments of the aspect, the tapered geometry of at least one of the plurality of transverse cuts forms chamfered inside faces of a pair of circumferentially extending rings adjacent to the at least one of the plurality of transverse cuts, wherein the chamfered inside faces meet flush when the tube member bends at an angle.

In various embodiments of the aspect, the tapered geometry of at least one of the plurality of transverse cuts comprises a taper angle (X) ranging from about 8 degrees to about 25 degrees.

In various embodiments of the aspect, the cut width at the inner surface of the tube member is equal to or less than 30 microns. In an embodiment, the cut width at the inner surface of the tube member is equal to or less than 10 microns. In an embodiment, the cut width at the inner surface ranges between 10 microns and 30 microns.

In various embodiments of the aspect, the cut width at the outer surface of the tube member is equal to or less than 47 microns. In an embodiment, the cut width at the outer surface of the tube member is equal to or less than 15 microns. In an embodiment, the cut width at the outer surface ranges between 15 microns and 47 microns.

In various embodiments of the aspect, the plurality of transverse cuts extend in a plane substantially perpendicular to a longitudinal axis of the tube member.

In various embodiments of the aspect, the plurality of transverse cuts comprise a one-beam cut pattern.

In various embodiments of the aspect, the plurality of transverse cuts comprise a two-beam cut pattern.

In various embodiments of the aspect, the plurality of transverse cuts comprise a three-beam cut pattern.

In various embodiments of the aspect, the tube member comprises a metallic tube.

In various embodiments of the aspect, the tube member comprises a polymeric tube.

In various embodiments of the aspect, the guidewire device further comprises a radiopaque coil between the tube member and the elongate core wire.

In another aspect, embodiments of the disclosure feature a method of making a guidewire device. In general, an embodiment of the method comprises the following steps:

- providing an elongate core wire;
- providing a tube member having an outer surface and an inner surface;
- forming a plurality of transverse cuts in the tube member at a plurality of axial locations of the tube member to create a plurality of circumferentially extending rings joined by a plurality of beams, wherein the plurality of transverse cuts are formed by using laser to remove more materials at the outer surface than at the inner surface of the tube member, forming the plurality of transverse cuts having a tapered geometry with a cut width at the outer surface being greater than a cut width at the inner surface; and coupling the tube member to a distal section of the elongate core wire.

In various embodiments of the aspect, the tapered geometry of at least one of the plurality of transverse cuts comprises a taper angle (X) that satisfies the following equation:

$$X = 2\ \arcsin[(c/2)/(r-b/2)]$$

wherein c represents the cut width of the at least one of the plurality of the transverse cuts at the inner surface, r represents an inner radius of the tube member, and b represents a beam height of the beam adjacent to the at least one of the plurality of the transverse cuts.

In various embodiments of the aspect, the tapered geometry of at least one of the plurality of transverse cuts comprises a taper angle ranging from about 8 degrees to about 25 degrees.

In various embodiments of the aspect, the laser is configured to provide a beam pulse having a focal angle equal to, or within 5 degrees greater or less than, the taper angle of the at least one of the plurality of transverse cuts.

In various embodiments of the aspect, the cut width at the inner surface of the tube member is equal to or less than 30 microns. In an embodiment, the cut width at the inner surface of the tube member is equal to or less than 10 microns. In an embodiment, the cut width at the inner surface ranges between 10 microns and 30 microns.

In various embodiments of the aspect, the cut width at the outer surface of the tube member is equal to or less than 47 microns.

In various embodiments of the aspect, the cut width at the outer surface of the tube member is equal to or less than 22 microns. In an embodiment, the cut width at the outer surface ranges between 15 microns and 47 microns. In an embodiment, the cut width at the outer surface ranges between 15 microns and 25 microns. In an embodiment, the cut width at the outer surface in a section of the tube member ranges between 23 microns and 47 microns.

In another aspect, embodiments of the disclosure feature a tube member for use in a medical device. In general, an embodiment of the tube member comprises a plurality of transverse cuts at a plurality of axial locations of the tube member, forming a plurality of circumferentially extending rings joined by a plurality of axially extending beams, wherein the plurality of transverse cuts comprises a tapered geometry with a cut width at the outer surface of the tube member being greater than a cut width at the inner surface of the tube member.

In various embodiments of the aspect, the tapered geometry of at least one of the plurality of transverse cuts comprises a taper angle (X) that satisfies the following equation:

$$X = 2\ \arcsin[(c/2)/(r-b/2)]$$

wherein c represents the cut width of the at least one of the plurality of the transverse cuts at the inner surface, r represents an inner radius of the tube member, and b represents a beam height of the beam adjacent to the at least one of the plurality of the transverse cuts.

In various embodiments of the aspect, the tapered geometry of at least one of the plurality of transverse cuts forms chamfered inside faces of a pair of circumferentially extending rings adjacent to the at least one of the plurality of transverse cuts, wherein the chamfered inside faces meet flush when the tube member bends at an angle.

In various embodiments of the aspect, the tapered geometry of at least one of the plurality of transverse cuts comprises a taper angle (X) ranging from about 8 degrees to about 25 degrees.

In various embodiments of the aspect, the cut width at the inner surface of the tube member is equal to or less than 30 microns. In an embodiment, the cut width at the inner surface of the tube member is equal to or less than 10 microns. In an embodiment, the cut width at the inner surface ranges between 10 microns and 30 microns.

In various embodiments of the aspect, the cut width at the outer surface of the tube member is equal to or less than 47 microns. In an embodiment, the cut width at the outer surface of the tube member is equal to or less than 22 microns. In an embodiment, the cut width at the outer surface ranges between 15 microns and 47 microns. In an embodiment, the cut width at the outer surface ranges between 15 microns and 25 microns. In an embodiment, the cut width at the outer surface in a section of the tube member ranges between 23 microns and 47 microns.

In various embodiments of the aspect, the plurality of transverse cuts extend in a plane substantially perpendicular to a longitudinal axis of the tube member.

In various embodiments of the aspect, the plurality of transverse cuts comprise a one-beam cut pattern.

In various embodiments of the aspect, the plurality of transverse cuts comprise a two-beam cut pattern.

In various embodiments of the aspect, the plurality of transverse cuts comprise a three-beam cut pattern.

In various embodiments of the aspect, the tube member comprises a metallic tube.

In various embodiments of the aspect, the tube member comprises a polymeric tube.

This Summary is provided to introduce selected aspects and embodiments of this disclosure in a simplified form and is not intended to identify key features or essential characteristics of the claimed subject matter, nor is it intended to be used as an aid in determining the scope of the claimed subject matter. The selected aspects and embodiments are presented merely to provide the reader with a summary of certain forms the invention might take and are not intended to limit the scope of the invention. Other aspects and embodiments of the disclosure are described in the section of Detailed Description.

These and various other aspects, embodiments, features, and advantages of the disclosure will become better understood upon reading of the following detailed description in conjunction with the accompanying drawings.

DETAILED DESCRIPTION OF EMBODIMENTS

With reference to the figures, various embodiments of a guidewire device and method of making guidewire devices will now be described. The figures are intended to facilitate description of embodiments of the disclosure and are not necessarily drawn to scale. Certain specific details may be set forth in the figures to provide a thorough understanding of the disclosure. It will be apparent to one of ordinary skill in the art that some of these specific details may not be employed to practice embodiments of the disclosure. In other instances, structures, components, systems, materials, and/or operations often associated with known medical procedures may not be shown or described in detail to avoid unnecessarily obscuring description of embodiments of the disclosure.

Embodiments of the disclosure provide a guidewire device comprising a tube member coupled to a distal section of an elongate core wire for reinforcement and improvement of performance. The tube member includes a plurality of transverse cuts with a pattern and/or geometry that provides the guidewire device with a desirable balance between bending flexibility, torsional rigidity, and tensile strength while still allowing the distal section of the guidewire device to achieve a tight bending radius without kinking. Embodiments of the disclosure also provide a method of making guidewire devices using laser to achieve a new cut geometry and processing speed unattainable by conventional techniques.

Figure 1:
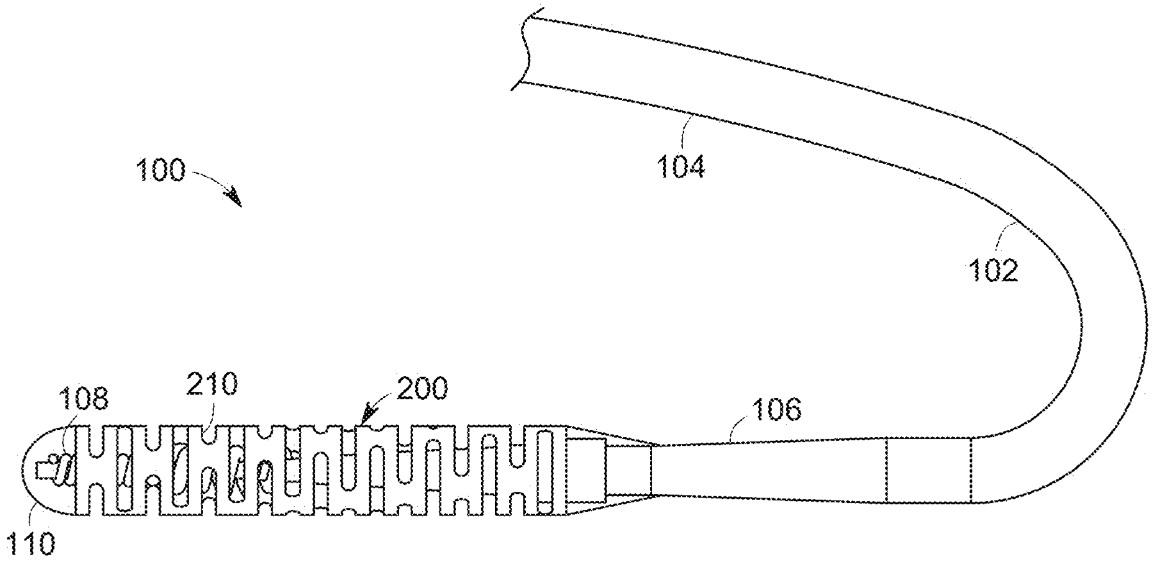
FIG. 1 is a simplified illustration of an example guidewire device according to embodiments of the disclosure.

FIG. 1 illustrates an example guidewire device 100 according to embodiments of the disclosure. The guidewire device 100 is generally configured for use in conjunction with a medical device to perform medical procedures. One example application of the guidewire device 100 of the disclosure is for guiding a catheter deep within the neuro vasculature. In a broad overview, the guidewire device 100 includes an elongate core wire 102 and a tube member 200 coupled to the core wire 102. The elongate core wire 102 extends between a proximal section 104 and a distal section 106 and has a length suitable for a particular application. The distal section 106 of the core wire 102 may be tapered towards the distal end to provide more bending flexibility. The proximal section 104 of the core wire 102 may have an increased diameter to maintain pushability and torsional rigidity of the guidewire device 100. The tube member 200 is disposed over the distal section 106 of the core wire 102. The tube member 200 can be coupled to the distal section 106 of the core wire 102 at one or more attachment points using e.g., adhesive, welding, soldering, etc. to allow transmission of torsional force from the proximal section 104 of the core wire 102 to the tube member 200 and/or from the tube member 200 to the distal section 106 of the core wire 102. In the space between the tube member 200 and the distal section 106 of the core wire 102, a radiopaque material 108 such as a platinum, gold, or other heavy metals in the form of e.g., a coil wound around and/or adhered to the core wire 102 can be provided for fluoroscope imaging. An atraumatic tip 110 e.g., in a round shape can be formed at the distal end of the guidewire device 100 to prevent damage to the vessel. According to embodiments of the disclosure, the tube member 200 includes a plurality of cuts 210 configured to improve the effectiveness of the guidewire device 100, e.g., providing a desirable balance between bending flexibility, torsional rigidity, and tensile strength, to be described in greater detail below.

Figure 2:
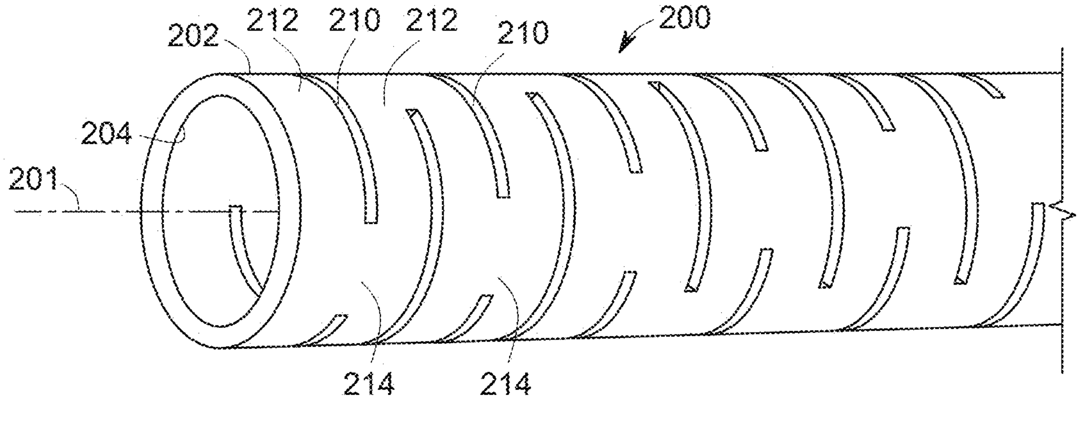
FIG. 2 is a simplified illustration of an example tube member that can be used as a guidewire device component according to embodiments of the disclosure.

With reference to FIG. 2, an example tube member 200 is shown to include a plurality of cuts or slots 210. The tube member 200 comprises an outer surface 202, an inner surface 204, and a thickness between the outer surface 202 and the inner surface 204. A plurality of transverse cuts 210 are formed at a plurality of axial locations of the tube member 200, forming a plurality of circumferentially extending rings 212 joined by a plurality of beams or axially extending beams 214. To facilitate description of various embodiments of the disclosure, the term "axial location" is used to refer to a location along a longitudinal axis 201 of the tube member 200. The term "transverse cut" 210 refers to a cut or slot in the tube member 200 that extends in a plane transverse to the longitudinal axis 201 of the tube member 200. A transverse cut 210 can be formed in a plane generally normal to the longitudinal axis 201 of the tube member 200. A transverse cut 210 can also be formed at an angle e.g., 5-45 degrees relative to a plane normal to the longitudinal axis 201 of the tube member 200. The term "cut width" may be used to refer to the width of the tube material removed or a gap created by the cutting. The term "circumferentially extending ring" 212 refers to an uncut, ring-shaped structure in the tube member 200 that extends circumferentially around the longitudinal axis 201 of the tube member 200. The term "beam" 214 refers to an uncut section in the tube member 200 that connects adjacent circumferentially extending rings 212. The term "axially extending beam" may be used interchangeably with the term "beam" as a beam extends along the longitudinal axis 201 of the tube member 200 in connecting the adjacent circumferentially extending rings. The term "beam height" may be used to refer to a dimension of a beam separating two adjacent transverse cuts in a plane.

Figure 3:
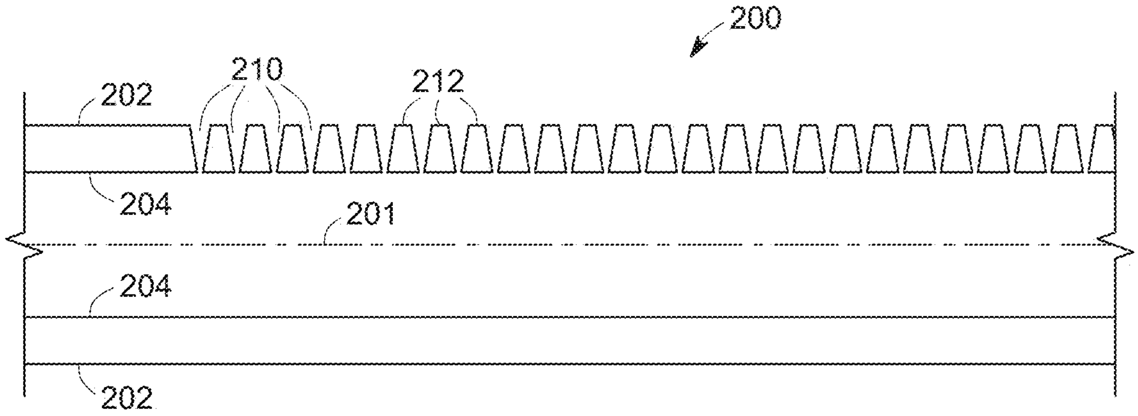
FIG. 3 is a cross-sectional side view of an example tube member including a plurality of tapered cuts according to embodiments of the disclosure.
Figure 5:
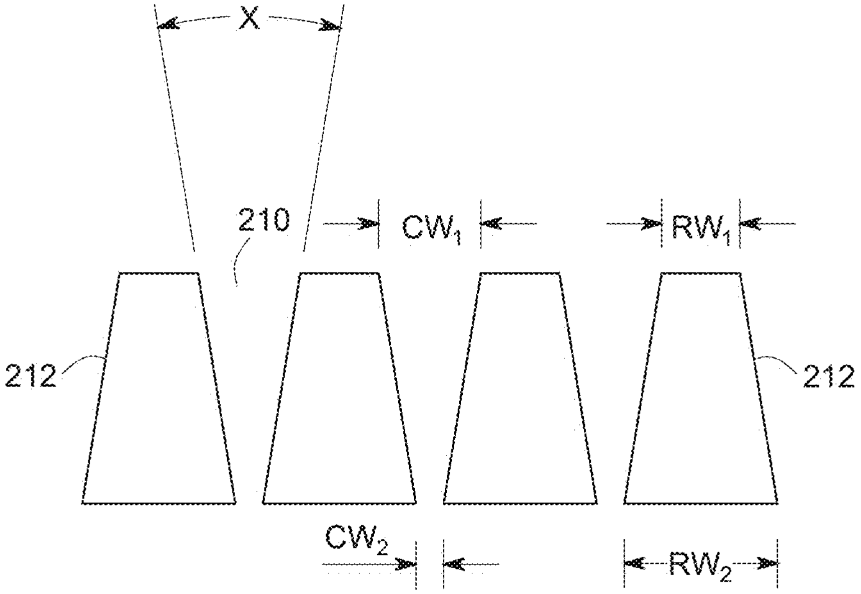
FIG. 5 illustrates an example tapered cut geometry according to embodiments of the disclosure.

With reference to FIGS. 3 and 5, according to embodiments of the disclosure the tube member 200 is provided with a plurality of transverse cuts 210 with a tapered geometry at a plurality of axial locations of the tube member 200. The transverse cuts 210 with a tapered geometry have a first cut width (CW1) at the outer surface 202 of the tube member and a second cut width (CW2) at the inner surface 204 of the tube member 200, wherein the first cut width (CW1) is greater than the second cut width (CW2), i.e., more tube material is removed from the outer surface 202 than from the inner surface 204 of the tube member 200. The plurality of transverse cuts 210 with a tapered geometry in the tube member 200 create a plurality of circumferentially extending rings 212 having a tapered geometry in a cross-section of the rings. The plurality of circumferentially extending rings 212 with a tapered geometry have a first ring width (RW1) at the outer surface 202 of the tube member 200 and a second ring width (RW2) at the inner surface 204 of the tube member 200, wherein the first ring width (RW1) is less than the second ring width (RW2).

With reference to FIG. 3, in an embodiment, a plurality of transverse cuts 210 with a tapered geometry are formed at a same side of the tube member 200, forming a plurality of circumferentially extending rings 212 at the same side. This arrangement allows the tube member 200 to bend at a preferred orientation and/or at a tighter bending radius, as shown FIG. 4.

Figure 4:
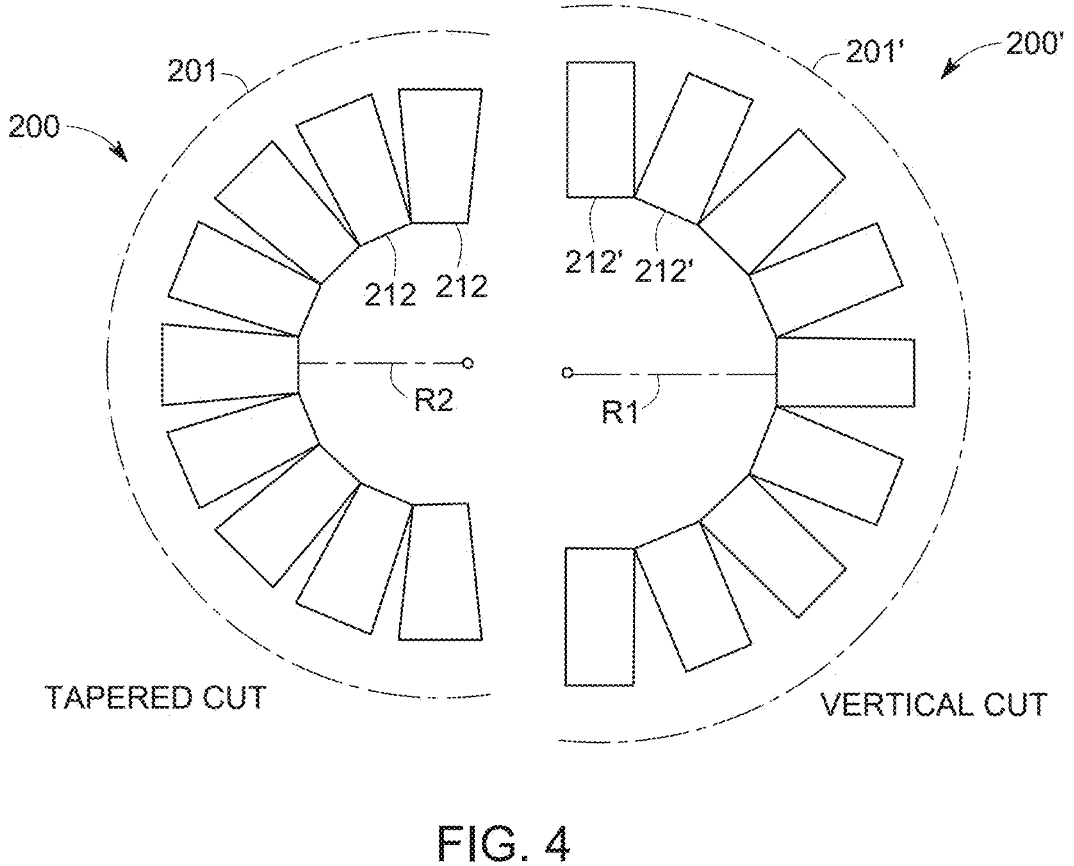
FIG. 4 compares the bending radii of a conventional tube member including a plurality of vertical cuts with a tube member including a plurality of tapered cuts according to embodiments of the disclosure.

FIG. 4 compares the bending radii of a tube member 200 of the disclosure (left panel) with a conventional tube member 200' (right panel), both having the same tube thickness. The tube member 200 of the disclosure is provided with a plurality of cuts having a tapered geometry, whereas the conventional tube member 200' is provided with a plurality of cuts having a vertical geometry. When the tube member 200 of the disclosure is flexed in a direction e.g., towards the side provided with the cuts 210, the circumferentially extending rings 212 will come closer together on the outer surface 202 side of the tube member 200, and spread apart on the inner surface 204 side of the tube member 200. Similarly, when the conventional tube member 200' is flexed in a direction towards the side provided with the cuts, the circumferentially extending rings 212' will come closer together on the outer surface side of the tube member 200', and spread apart on the inner surface side of the tube member 200'. If the tube members 200, 200' are flexed far enough, the rings 212, 212' will collide at the outer surface side, preventing the tube members 200, 200' from bending any further without kinking. The conventional tube member 200' provided with a plurality of vertical cuts 212' allows flexion at a radius of R1. With tapered cuts 210 where more materials are removed from the outer surface 202 of the tube member 200 according to the disclosure, the adjacent rings 212 have more clearance at the outer surface 202 of the tube member 200, thus allowing the tube member 200 to flex far further before the rings 212 collide at the outer surface 202 of the tube member 200, thereby allowing the tube member 200 to bend at a tighter or smaller radius R2.

With reference to FIG. 5, an example tapered geometry of transverse cuts 210 and/or circumferentially extending rings 212 are shown according to embodiments of the disclosure. The non-parallel sides or legs of the trapezoidal geometry of adjacent circumferentially extending rings 212 form a taper angle (X) of the transverse cuts 210. A greater taper angle (X) would provide more clearance for the circumferentially extending rings 212 to flex before the rings 212 collide at the outer surface 202 of the tube member 200. According to embodiments of the disclosure, the taper angle (X) of the transverse cuts 210 may range between 8 and 25 degrees. Other considerations for choosing a proper taper angle (X) include the diameter and thickness of the tube member 200, and the desired flexion radius (R) of the tube member 200, etc. According to embodiments of the disclosure, the taper angle (X) of the plurality of the transverse cuts 210 is chosen to allow the tube member 200 to bend at least in 180 degrees, or 270 degrees, or in 360 degrees, or any angle between 180 and 360 degrees without kinking.

According to embodiments of the disclosure, the cut width of a plurality of transvers cuts at the outer surface (CW1) is equal to or less than 47 microns, or equal to or less than 22 microns. In some embodiments, the cut width at the outer surface (CW1) is equal to or less than 55 microns. According to embodiments of the disclosure, the cut width at the outer surface (CW1) ranges between 15 microns and 47 microns, or between 15 microns and 25 microns. In an embodiment, the cut width at the outer surface in a section of the tube member ranges between 23 microns and 47 microns. The cut width at the outer surface (CW1) can be substantially constant along the cut.

According to embodiments of the disclosure, the cut width of a plurality of transvers cuts at the inner surface (CW2) is equal to or less than 30 microns. According to embodiments of the disclosure, the cut width at the inner surface (CW2) ranges between 10 microns and 30 microns. The cut width at the inner surface (CW2) can be substantially constant along the cut.

Figure 6:
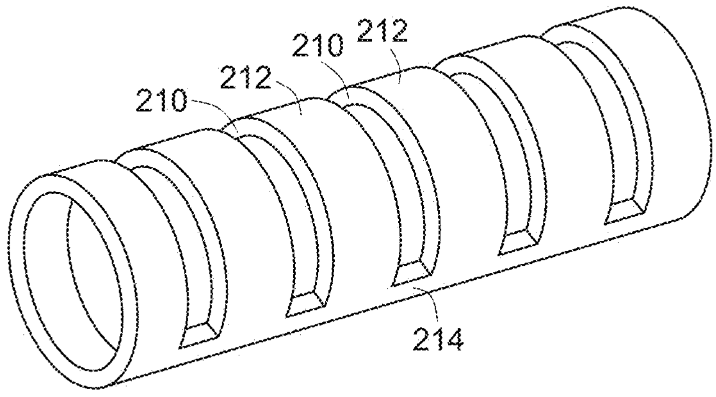
FIG. 6 is a simplified illustration of a tube member including a plurality of cuts in a one-beam cut pattern according to embodiments of the disclosure.

According to embodiments of the disclosure, a plurality of transverse cuts 210 with a tapered geometry are formed in a one-beam cut pattern. In a one-beam cut pattern, a single axially extending beam 214 joins a pair of adjacent circumferentially extending rings 212. FIG. 6 illustrates an example of a one-beam cut pattern. In the example shown in FIG. 6, a series of beams 214 are arranged e.g., aligned on a same side of the tube member, forming a preferred bending direction of the tube member. In alternative embodiments, each successive beam 214 can be rotationally offset by an angle ranging e.g., between 5 and 180 degrees from the preceding beam and/or the subsequent beam. The successive beams may offset in a linear helical pattern at a constant offset angle, or at a non-linear pattern at a random offset angle, or a combination thereof at different sections of the tube member.

Figure 7:
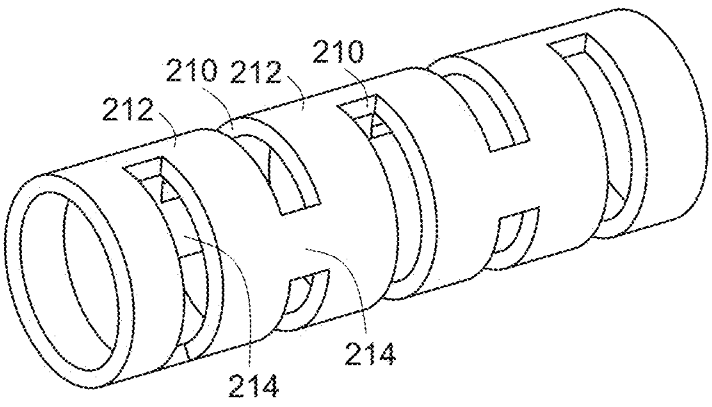
FIG. 7 is a simplified illustration of a tube member including a plurality of cuts in a two-beam cut pattern according to embodiments of the disclosure.

According to embodiments of the disclosure, a plurality of transverse cuts 210 with a tapered geometry are formed in a two-beam cut pattern. In a two-beam pattern, two axially extending beams 214 are formed between a pair of adjacent circumferentially extending rings 212. FIG. 7 illustrates an example of a two-beam cut pattern. In the example shown in FIG. 7, a beam pair 214 is arranged symmetrically, or the two beams 214 of a beam pair are circumferentially equally spaced apart (opposite to each other in 180 degrees). Alternatively, a beam pair can be arranged non-symmetrically, i.e., the two beams 214 of a beam pair are brought closer together circumferentially (less than 180 degrees) or spaced apart farther (greater than 180 degrees). In the example shown in FIG. 7, a beam pair is arranged rotationally offset from the preceding and/or the subsequent beam pair in 90 degrees. Alternatively, the offset angle can be any angle between 1 and 90 degrees. Further, the successive beam pairs may offset either in a linear helical pattern or in a non-linear pattern, or a combination thereof in different sections of the tube member. In some embodiments, a series of beam pairs are arranged to align in a same plane.

Figure 8:
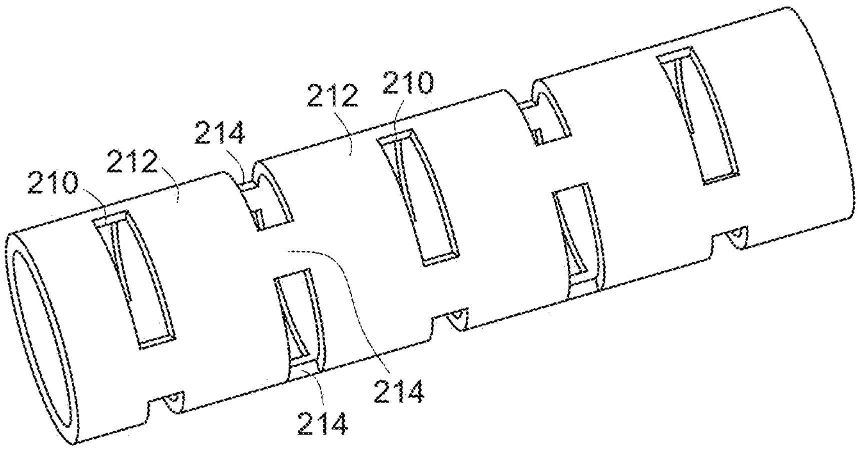
FIG. 8 is a simplified illustration of a tube member including a plurality of cuts in a three-beam cut pattern according to embodiments of the disclosure.

According to embodiments of the disclosure, a plurality of transverse cuts 210 with a tapered geometry are formed in a three-beam cut pattern. In a three-beam cut pattern, three beams 214 ("beam group") are formed between a pair of adjacent circumferentially extending rings 212. FIG. 8 illustrates an example of a three-beam cut pattern. Like a two-beam cut pattern, the beams 214 in a three-beam cut pattern can be symmetrically formed e.g., circumferentially spaced apart equally in 120 degrees, or non-symmetrically formed. Similarly, a beam group in a three-beam cut pattern can be arranged rotationally offset from the preceding and/or the subsequent beam group at an offset angle between 1-90 degrees. The successive beam groups may offset in a linear helical pattern, or a non-linear pattern, or a combination thereof in different sections of the tube member.

Embodiments of the disclosure provides a method of making guidewire devices. The method utilizes laser to cut a tube member in a pattern and/or geometry unattainable by the conventional techniques. The novel cutting pattern and/or geometry provides the guidewire device with a desired balance between bending flexibility, torsional rigidity, and tensile strength. Beneficially, the cutting geometry allows the inside faces of adjacent circumferentially extending rings to meet flush when being flexed, thereby allowing the guidewire device to bend at a tighter radius without kinking or deformation.

Figure 9:
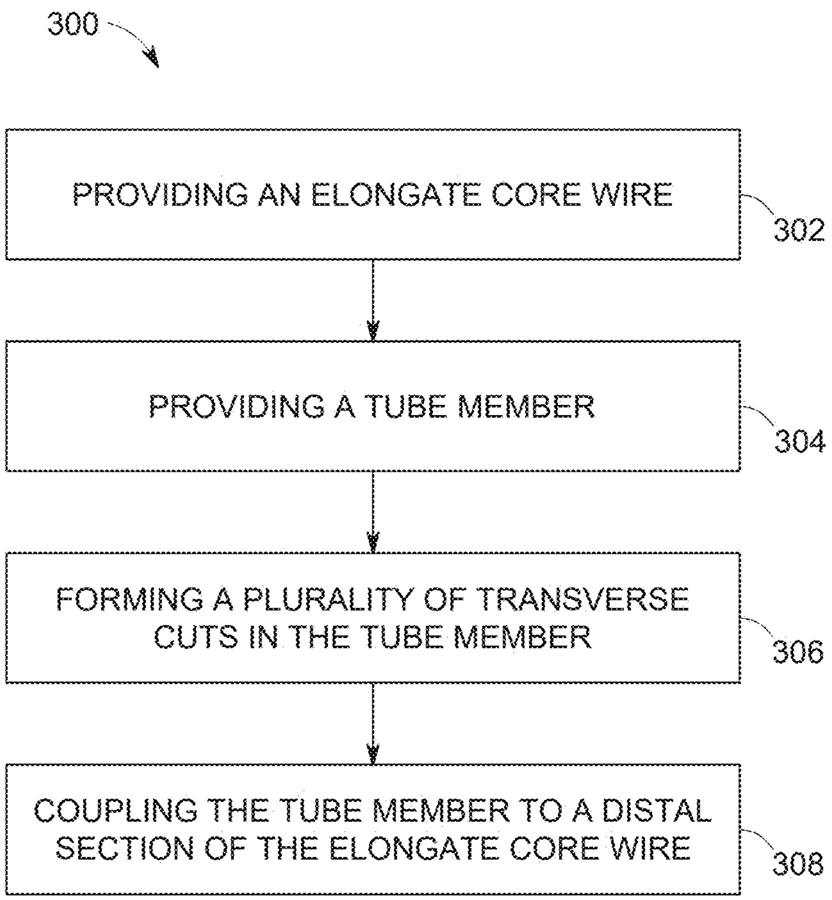
FIG. 9 is a flow chart illustrating example steps of a method of making a guidewire device according to embodiments of the disclosure.

FIG. 9 is a flowchart illustrating example steps of a method 300 of making a guidewire device according to embodiments of the disclosure. At step 302, an elongate core wire is provided. The core wire may be made of metal, such as stainless steel, titanium, nickel titanium alloys or Nitinol, or other biocompatible material. The core wire may be a single continuous wire extending substantially the entire axial length of the guidewire device. The core wire may also be a multi-piece or multi-region construction wherein each piece or region is made of different materials having different properties such as flexibility or rigidity. For example, the proximal section or region of the core wire may be made of relatively stiff stainless steel for better pushability and torqueability whereas the distal section of the core wire can be made of relatively elastic Nitinol for better steerability and trackability. The core wire may be solid, hollow, or have some other interior construction.

The core wire may have a length sufficient for reaching to a target site within the patient. Generally, the length of the core wire ranges between 200 cm and 320 cm. The distal section of the core wire may be tapered towards the distal end to provide more bending flexibility. The tapered distal section of the core wire may have a round, rectangular, or other regular or irregular cross-sectional shape. The proximal section of the core wire may have an increased diameter to maintain pushability and torsional rigidity of the guidewire device. Alternatively, the core wire has a circular cross-section and/or a constant diameter.

In some embodiments, the distal section of the core wire is wound with a radiopaque coil for fluoroscopy imaging. Suitable materials for the radiopaque coil include platinum, gold, or other heavy metals.

At step 304, a tube member is provided. The tube member may be made of a metal, metal alloy, polymer, metal-polymer composite, or any combination thereof. Suitable metals and metal alloys for the tube member include stainless steel, nickel-titanium alloy or Nitinol, or other nickel alloys such as cobalt-chromium alloys, nickel-molybdenum alloys, nickel-copper alloys, nickel-cobalt alloys, other nickel-iron alloys, nickel-tungsten alloys, cobalt-chromium-molybdenum alloys, and so on. Suitable polymers for the tube member include polytetrafluoroethylene (PTFE), fluorinated ethylene propylene (FEP), and other suitable polymeric materials.

The tube member may have a length suitable as a component to be coupled to the distal section of the core wire of the guidewire device. For example, the tube member may have a length ranging e.g., from 10 cm to 55 cm for application in a guidewire device. It should be noted that embodiments of the disclosure can find applications in making other medical devices such as a catheter device, which can have a length suitable for application as a catheter device.

The tube member may have an outer diameter, an inner diameter, and a wall thickness selected to provide one or more desired base properties, such as rigidity, flexibility, tensile strength, torque response etc. for a particular application. In general, if the outer diameter of the tube member is increased while the wall thickness is decreased, the tube member can have the same bending stiffness with an increased torque response, at the cost of some mechanical strength. In another example, if the outer diameter of the tube is decreased while the wall thickness is increased, the tube member can have increased axial rigidity with the same bending stiffness, at the cost of reduced torque response.

At step 306, a plurality of transverse cuts or slots are formed in the tube member at a plurality of axial locations of the tube member. The plurality of transverse cuts formed in the tube member create a plurality of circumferentially extending rings joined by a plurality of axially extending beams.

According to embodiments of the disclosure, laser is used to form the plurality of cuts or slots in the tube member. Laser beams or pulses can cut or remove materials from a thin tubular part or tube member with high precision and resolution, creating no mechanical deformation or burrs. According to embodiments of the disclosure, micron- or submicron-sized patterns and/or geometries are formed with laser pulses. The laser cutting process can be automated or configured with a computer software for efficient high-speed processing.

Various types of lasers are available in the art and can be selected for use in the method of making guidewire devices of the disclosure. According to embodiments of the disclosure, a gas-assist laser is used to cut the tube member in which a pressurized gas jet or assist gas, is utilized to blow away molten material, cools the material, and prevents it from warping or re-solidifying to improve the quality and efficiency of the cutting process.

The duration, frequency, shape, and other parameters of the laser pulses can be set or selected based on the cut dimensions, geometries, and cutting speed, etc. If the tube member is thin, a high pulse frequency and short pulse duration can be used. Pulse duration is the elapsed time between the beginning and the end of a single pulse of energy, measured in seconds. The shorter the pulse duration, the greater the effectiveness of the cut, with fewer burrs or defects, such as heat-affected zones. Ultrashort pulses ranging from tens of picoseconds to femtoseconds can be used in embodiments of the disclosure.

A stage can be used to hold and/or move the tube member during the cutting process. The stage can be controlled by a precision motor system, which can translate and/or rotate the tube member at a micron or sub-micron precision level. For example, in the cutting process the tube member can be held and/or moved by the stage while beam pulses from a laser source are aimed at and deposited on the tube member. In some embodiments, the laser source including a chain of optics which can be controlled and/or adjusted during the cutting process while the tube member is being held and/or moved by the stage.

In an embodiment, the tube member is held at a fixed axial location. A laser source can be actuated to deposit pulses of beams on to the tube member while the tube member is being rotated or turned at the fixed axial location, forming a cut with a predetermined cut width and/or length. The cut can be a transverse cut formed in a plane normal to the longitudinal axis of the tube member, or in a plane at an angle to the plane normal to the longitudinal axis of the tube member. After the desired length of a cut (as measured by degrees) is achieved, the laser source can be turned off.

In an embodiment, the tube member is held at a first axial location. Pulses of laser beam can be deposited to the tube member while the tube member is being rotated at the first axial location. A first transverse cut is formed at the first axial location of the tube member. Then, the tube member is translated to a second axial location. Pulses of laser beam can be deposited to the tube member while the tube member is being rotated at the second axial location. A second transverse cut is formed at the second axial location of the tube member. In this manner, a plurality of transverse cuts can be formed in the tube member at a plurality of axial locations.

In an embodiment, the tube member is translated from a first axial location to a second axial location and rotated during the translation. Pulses of laser beam can be deposited to the tube member while the tube member is being translated and rotated simultaneously. In this manner, a helical cut can be formed in the tube member extending between the first axial location and the second axial location of the tube member. The laser source can be turned on and off while the tube member is being translated and rotated simultaneously to form a plurality of helical cuts.

In an embodiment, the laser source can be configured to provide pulses of beam suitable for cutting the tube member with a tapered geometry. For example, the laser source can be configured to deposit pulses of beam having a suitable focal point, allowing more tube material to be removed at the outer surface than at the inner surface of the tube member, thereby forming a cut having a tapered geometry with the cut width at the outer surface being greater than the cut width at the inner surface.

Figure 10A:
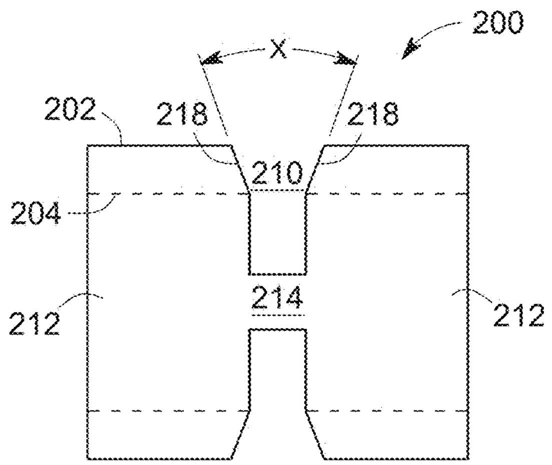
FIG. 10A is a simplified illustration showing a side view of a tapered cut in a tube member according to embodiments of the disclosure.
Figure 10B:
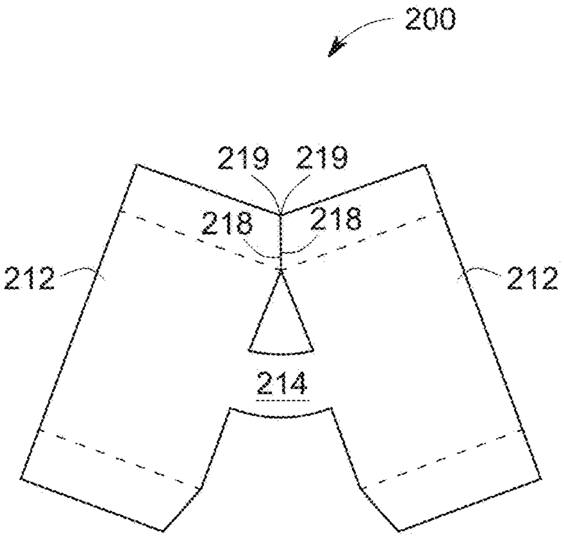
FIG. 10B schematically shows the bending of the tube member of FIG. 10A when in use.
Figure 11A:
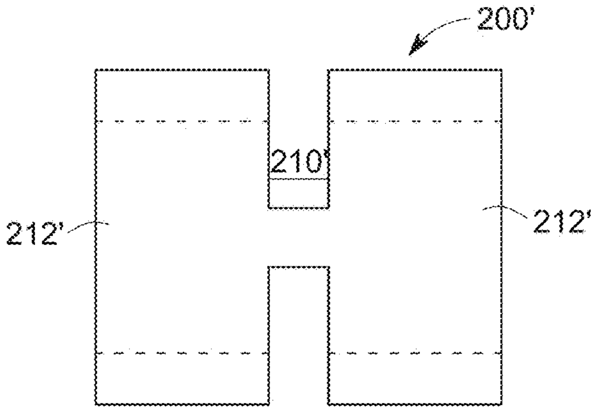
FIG. 11A is a simplified illustration showing a side view of a vertical cut in a tube member for comparison.
Figure 11B:
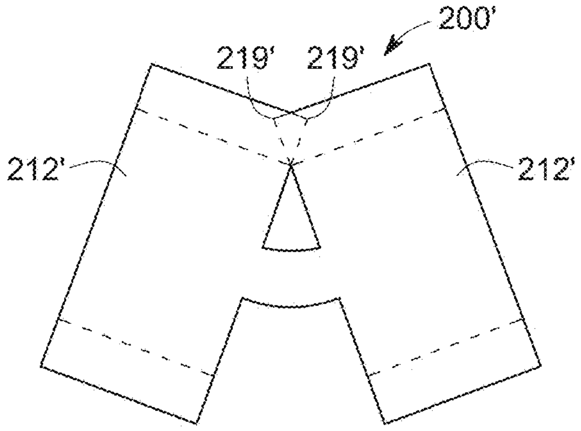
FIG. 11B schematically shows the bending of the tube member of FIG. 11A when in use.

A cut with a tapered geometry is beneficial as the inside faces or surfaces of adjacent circumferentially extending rings can meet in a flush manner, thus allowing the tube member to bend with a tighter bending angle without kinking or deformation. FIG. 10A is a cross-sectional side view of a tube member 200 provided with a cut 210 having a tapered geometry according to embodiments of the disclosure. As shown, the tube member 200 has an outer surface 202 and an inner surface 204. A cut 210 in the tube member 200 forms two circumferentially extending rings 212 connected by an axially extending beam 214. The cut 210 has a tapered geometry through the thickness of the tube member 200 between the outer surface 202 and inner surface 204. The chamfered surfaces or inside faces 218 of the adjacent circumferentially extending rings 212 form a taper angle (X). As shown in FIG. 10B, when the tube member 200 is maximally flexed, the inside faces 218 of the adjacent rings 212 meet flush, allowing the outer edges 219 of the adjacent rings 212 to contact without deformation when the tube member 200 maximally bends. This contrasts to a conventional straight or vertical cut 210' formed in a tube member 200' shown in FIGS. 11A-11B, where the edges 219' of adjacent circumferentially extending rings 212' would collide or prevent the tube member 200' from bending at the same maximal bending angle as in FIGS. 10A-10B without kinking or deformation.

Figure 12:
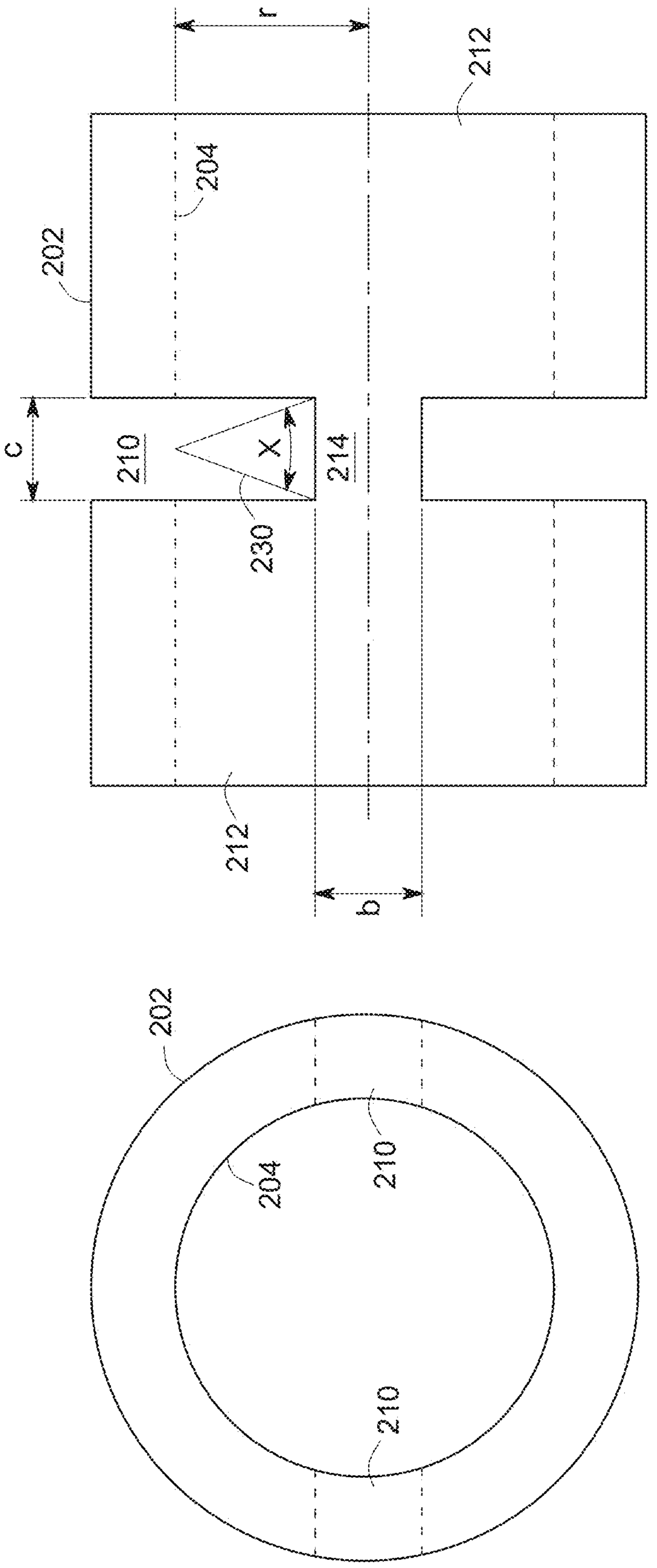
FIG. 12 is a simplified illustration showing some parameters of a cut in a tube member.

With reference to FIG. 12, according to embodiments of the disclosure, a proper taper angle (X) of a cut 210 can be determined by drawing an isosceles triangle 230, where the height of the triangle 230 is equal to the inner radius (r) of the tube member 200 minus half of the height (b) of an axially extending beam 214, and the base of the triangle is the cut width (c) at the inner surface 204 of the tube member 200. This assumes that the adjacent circumferentially extending rings 212 connected by the axially extending beam 214 makes contact at the inner diameter 204 of the tube member 200 when flexed, thereby forming the triangle 230. This gives the following equation:

$$X = 2\ \arcsin[(c/2)/(r - b/2)]$$

wherein X represents the taper angle, c represents the cut width at the inner surface of the tube member, r represents an inner radius of the tuber member, and b represents the height of the beam adjacent to the cut. Once the taper angle (X) is determined based on the desired cut width (c) and a beam height (b) on a given tube member (r) according to the above equation, it can be used as a target or guide to select or configure the chain of optics in the laser source to provide pulses of laser beam having a proper focal angle to perform the cutting.

Figure 13:
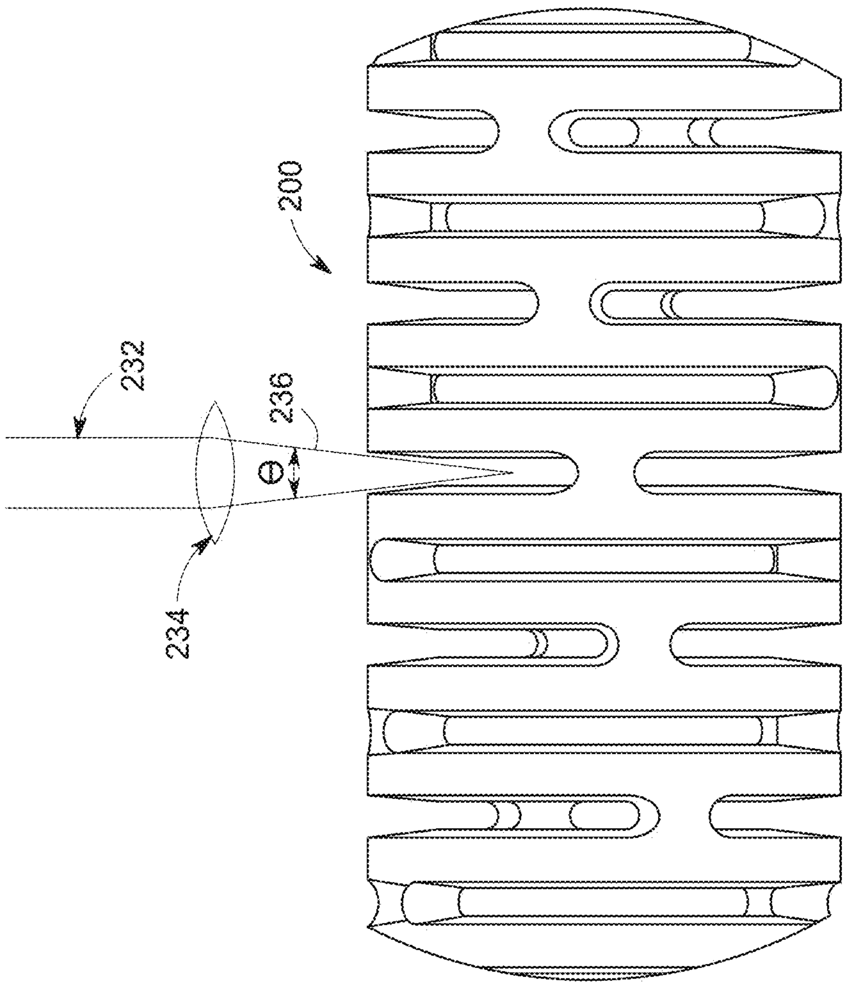
FIG. 13 illustrates an example laser beam deposited on to a tube member to form a tapered cut according to embodiments of the disclosure.

FIG. 13 schematically shows a collimated laser beam 232 shaped by a chain of optics (not shown) passes through a focusing lens 234, forming a laser beam 236 with a focal angle (θ). The focused laser beam 236 is deposited to the tube member 200 to form a through cut, where more tube material is removed at or adjacent to the outer surface of the tube member than at or adjacent to the inner surface of the tube member, forming a tapered geometry through the thickness of the tube member.

Figure 14:
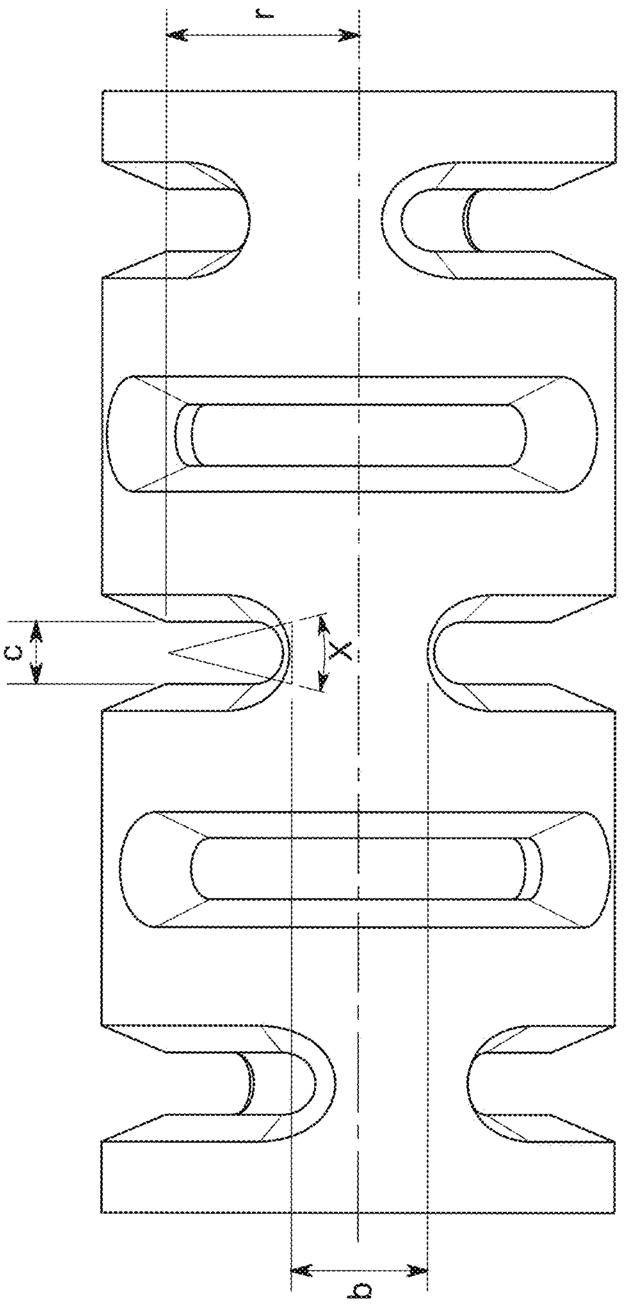
FIG. 14 is a simplified illustration of a tube member showing some details of a tapered cut geometry according to embodiments of the disclosure.

According to embodiments of the disclosure, the optics of the laser source can be arranged or selected to provide a laser beam with a focal angle (θ) substantially equal to the taper angle (X) of the cut to be formed in the tube member. According to some embodiments of the disclosure, the optics of the laser source can be arranged or selected to provide a laser beam with a focal angle (θ) within five degrees greater or less (+/−) 5° than the taper angle (X) of the cut to be formed in the tube member, to accommodate to the variance in focus and cutting power of the laser beam. FIG. 14 is an enlarged view of a section of the tube member cut by a laser beam having a focal angle (θ), with cutting features and parameters (r, c, b, X) shown according to embodiments of the disclosure.

According to embodiments of the disclosure, the chain of optics of the laser source are arranged or configured to provide pulses of laser beam to form cuts with a taper angle (X) ranging from about 8 to about 25 degrees.

According to embodiments of the disclosure, the chain of optics of the laser source are arranged or configured to provide pulses of laser beam to form cuts in the tube member with a cut width at the outer surface equal to or less than 47 microns. In some embodiments, the cut width at the outer surface is equal to or less than 22 microns. In an embodiment, the cut width at the outer surface ranges between 15 microns and 47 microns. In an embodiment, the cut width at the outer surface ranges between 15 microns and 25 microns. In an embodiment, the cut width at the outer surface in a section of the tube member ranges between 23 microns and 47 microns.

According to embodiments of the disclosure, the chain of optics of the laser source are arranged or configured to provide pulses of laser beam to form cuts in the tube member with a cut width at the inner surface equal to or less than 30 microns. In some embodiments, the cut width at the inner surface is equal to or less than 10 microns. According to embodiments of the disclosure, the cut width at the inner surface ranges between 10 microns and 30 microns.

Returning to FIG. 9, at step 308, the tube member is coupled to the distal section of the elongate core wire. The tube member can be coupled to the distal section of the core wire by using e.g., adhesive, welding, soldering, etc., at one or more attachment points.

The cutting process can be automated with a computer software, which can be configured or programmed to control the movement of the stage supporting the tube member and/or the operation of the laser source providing beam pulses.

EXAMPLE

A laser source commercially available was used to cut a tube member supported by a stage controlled by a system of motors. The tube member had an outer diameter of 0.013 inches, an inner diameter 0.0096 inches, and a length of 35 cm. A series of cuts were formed in the tube member, with a cut width of 31 microns at the outer diameter and a cut width of 14 microns at the inner diameter. The cuts have a tapered geometry with a taper angle of 22°. The cut length ranges from about 160° at the tip end where a tight bending radius was desired, to about 63° at the other end. Over 5000 cuts were created in the tube member, in which 616 cuts were within the section of 1 cm from the tip end where a tight bending radius was desired.

Various embodiments of a guidewire device and a method of making guidewire devices have been described with reference to figures. It should be noted that an aspect described in conjunction with a particular embodiment is not necessarily limited to that embodiment and can be practiced in any other embodiments. The figures are intended for illustration of embodiments but not for exhaustive description or limitation on the scope of the disclosure. Alternative structures, components, and materials will be readily recognized as being viable without departing from the principle of the claimed invention. Further, while some embodiments of the disclosure are described in conjunction with a guidewire device, this is not intended to be limiting. For example, the tube member including transverse cuts with a tapered geometry can be configured or used as a catheter device, and/or as a component for other interventional devices.

All technical and scientific terms used herein have the meaning as commonly understood by one of ordinary skill in the art unless specifically defined otherwise. As used in the description and appended claims, the singular forms of "a," "an," and "the" include plural references unless the context clearly dictates otherwise. The term "or" refers to a nonexclusive "or" unless the context clearly dictates otherwise. The term "proximal" and its grammatically equivalent refers to a position, direction or orientation towards the user or physician's side. The term "distal" and its grammatically equivalent refers to a position, direction, or orientation away from the user or physician's side. The designations "rearward," "forward," and the like are not meant to limit the referenced component to a specific orientation. It will be appreciated that such designations refer to the orientation of the referenced component as illustrated in the Figures; the systems and devices of the disclosure can be used in any orientation suitable to the user. The term "first" or "second" etc. may be used to distinguish one element from another in describing various similar elements. It should be noted the terms "first" and "second" as used herein include references to two or more than two. Further, the use of the term "first" or "second" should not be construed as in any particular order unless the context clearly dictates otherwise. The order in which the method steps are performed may be changed in alternative embodiments. One or more method steps may be skipped altogether, and one or more optional steps may be included. All numeric values are provided for illustration and assumed to be modified by the term "about," whether explicitly indicated or not. The term "about" generally refers to a range of numbers that one of skill in the art would consider equivalent to the recited value e.g., having the same function or result. The term "about" may include numbers that are rounded to the nearest significant figure. The recitation of a numerical range by endpoints includes all numbers within that range.

Those skilled in the art will appreciate that various other modifications may be made. All these or other variations and modifications are contemplated by the inventors and within the scope of the invention.

What is claimed is:

1. A guidewire device comprising:

an elongate core wire extending between a proximal section and a distal section; and a tube member over the distal section of the elongate core wire, the tube member having an outer surface and an inner surface, wherein the tube member comprises a plurality of transverse cuts at a plurality of axial locations of the tube member, forming a plurality of circumferentially extending rings joined by a plurality of beams, wherein the plurality of transverse cuts comprises a tapered geometry with a cut width at the outer surface of the tube member being greater than a cut width at the inner surface of the tube member, the tapered geometry of at least one of the plurality of transverse cuts comprises a taper angle (X) ranging from 8 degrees to 25 degrees, and the tapered geometry of at least one of the plurality of transverse cuts forms chamfered inside faces of a pair of circumferentially extending rings adjacent to the at least one of the plurality of transverse cuts, wherein the chamfered inside faces meet flush when the tube member bends at an angle.

2. The guidewire device of claim 1, wherein the tapered geometry of at least one of the plurality of transverse cuts comprises the taper angle (X) that satisfies the following equation:

$$X = 2\ \arcsin\left[(c/2)/(r - b/2)\right]$$

wherein c represents the cut width of the at least one of the plurality of the transverse cuts at the inner surface, r represents an inner radius of the tube member, and b represents a beam height of a beam adjacent to the at least one of the plurality of the transverse cuts.

3. The guidewire device of claim 1, wherein the cut width at the inner surface of the tube member ranges between 10 microns and 30 microns.

4. The guidewire device of claim 1, wherein the cut width at the outer surface of the tube member ranges between 15 microns and 47 microns.

5. The guidewire device of claim 1, wherein the cut width at the outer surface of the tube member ranges between 15 microns and 25 microns.

6. The guidewire device of claim 1, wherein the plurality of transverse cuts extend in a plane substantially perpendicular to a longitudinal axis of the tube member.

7. The guidewire device of claim 1, wherein the plurality of transverse cuts comprise a one-beam cut pattern.

8. The guidewire device of claim 1, wherein the plurality of transverse cuts comprise a two-beam cut pattern.

9. The guidewire device of claim 1, wherein the plurality of transverse cuts comprise a three-beam cut pattern.

10. The guidewire device of claim 1, wherein the tube member comprises a metallic tube.

11. The guidewire device of claim 1, wherein the tube member comprises a polymeric tube.

12. The guidewire device of claim 1, further comprising a radiopaque coil between the tube member and the elongate core wire.

* * * * *